(12) United States Patent
Gabbay (10) Patent No.: US 7,160,322 B2
(45) Date of Patent: Jan. 9, 2007

(54) IMPLANTABLE CARDIAC PROSTHESIS FOR MITIGATING PROLAPSE OF A HEART VALVE

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 421 days.

(21) Appl. No.: 10/639,970

(22) Filed: Aug. 13, 2003

(65) Prior Publication Data

US 2005/0038508 A1 Feb. 17, 2005

(51) Int. Cl.
*A61F 2/06* (2006.01)
(52) U.S. Cl. .................................. 623/2.36; 623/2.11
(58) Field of Classification Search ....... 623/2.36–2.38
See application file for complete search history.

(56) References Cited

U.S. PATENT DOCUMENTS

| | | |
|---|---|---|
| 4,042,979 A | 8/1977 | Angell |
| 4,084,268 A | 4/1978 | Ionescu et al. |
| 4,240,161 A | 12/1980 | Huffstutler et al. |
| 4,350,492 A | 9/1982 | Wright et al. |
| 4,477,930 A | 10/1984 | Totten et al. |
| 4,491,986 A | 1/1985 | Gabbay |
| 4,725,274 A | 2/1988 | Lane et al. |
| 4,759,758 A | 7/1988 | Gabbay |
| 5,258,021 A | 11/1993 | Duran |
| 5,411,552 A | 5/1995 | Andersen et al. |
| 5,500,014 A | 3/1996 | Quijano et al. |
| 5,549,665 A | 8/1996 | Vesely et al. |
| 5,584,879 A | 12/1996 | Reimold et al. |
| 5,800,527 A | 9/1998 | Jansen et al. |
| 5,840,081 A | 11/1998 | Andersen et al. |
| 5,855,602 A | 1/1999 | Angell |
| 5,861,028 A | 1/1999 | Angell |
| 5,948,017 A | 9/1999 | Taheri |
| 6,168,614 B1 | 1/2001 | Andersen et al. |
| 6,419,695 B1 | 7/2002 | Gabbay |
| 2003/0083742 A1* | 5/2003 | Spence et al. ............. 623/2.16 |

FOREIGN PATENT DOCUMENTS

EP 0850607 7/1998

OTHER PUBLICATIONS

"Nitinol Solutions", Product brochure of Raychem Corporation, Electronics OEM Components Division Menlo Park, California Copyright date of 1999.

\* cited by examiner

*Primary Examiner*—Thomas Barrett
(74) *Attorney, Agent, or Firm*—Tarolli, Sundheim, Covell & Tummino LLP (57) ABSTRACT

An apparatus helps improve operation of a heart valve. The apparatus includes an arcuate base portion having a central axis and a buttress extending from the base portion axially relative to the base portion. The buttress has a first surface and an opposite second surface. The first surface is dimensioned and configured to be engaged by a first leaflet of the heart valve when the apparatus is implanted in the heart valve. The second surface is dimensioned and configured to be engaged by a second leaflet of the heart valve when the apparatus is implanted in the heart valve. The buttress permits flow of blood adjacent both the first surface of the buttress and the second surface of the buttress when the first and second leaflets are not engaging the buttress.

23 Claims, 6 Drawing Sheets

IMPLANTABLE CARDIAC PROSTHESIS FOR MITIGATING PROLAPSE OF A HEART VALVE

TECHNICAL FIELD

The present invention relates to an implantable cardiac prosthesis and, more particularly, to a prosthesis that can be implanted to mitigate prolapse of a heart valve.

BACKGROUND

A heart valve may become defective or damaged from degeneration caused by congenital malformation, disease, aging, etc. When the valve becomes defective or damaged, the leaflets may not function properly to effectively stop blood flow when appropriate. One common problem associated with a degenerating heart valve is an enlargement, or dilation, of the valve annulus. These and other conditions can cause one or more of the leaflets to prolapse.

For example, when a mitral valve functions properly, the mitral valve prevents regurgitation of blood from the left ventricle into the left atrium when the ventricle contracts. In order to withstand the substantial backpressure and prevent regurgitation of blood into the left atrium during the ventricular contraction, the cordae tendinae hold the anterior and posterior leaflets in place across the opening of the annular ring. The cordae tendinae are fibrous cords that anchor the leaflets to the muscular wall of the heart and control the movement of the leaflets.

If the annulus of the mitral valve enlarges or dilates to a point where the attached leaflets are unable to fully close (malcoaptation) the opening, regurgitation may occur. Further, valve prolapse, or the forcing of the valve annulus and leaflets into the left atrium by backpressure in the left ventricle, may occur. Adverse clinical symptoms, such as chest pain, cardiac arrhythmias, dyspnea, may manifest in response to regurgitation or valve prolapse. As a result, surgical correction, either by valve repair procedures or by valve replacement, may be required.

Surgical reconstruction or repair procedures may include plication, chordal shortening, or chordal replacement. Another common repair procedure relates to remodelling of the valve annulus (e.g., annuloplasty), which may be accomplished by implantation of a prosthetic ring to help stabilize the annulus and to correct or help prevent valve insufficiency which may result from a defect or dysfunction of the valve annulus. Properly sizing and implanting an annuloplasty ring may substantially restore the valve annulus to its normal, undilated, circumference. In situations where the valve leaflets exhibit lesions, reconstruction of one or more valve leaflets by securing grafts or patches to the leaflets, such as over lesions or holes formed in the leaflet, may be necessary. The repair or reconstruction of the leaflets may be complicated and time consuming, the results of which are not readily reproducible.

SUMMARY

The present invention relates generally to a cardiac prosthesis, or apparatus, that may be implanted at an annulus of a heart valve to help improve operation of a defective or damaged heart valve. The apparatus provides a buttress that extends from a base portion, such as in a substantially axial direction relative to the base portion. The base portion may be generally annular or C-shaped. The buttress The apparatus also may be formed of a material that can be manipulated to a reduced cross-sectional condition to facilitate implantation of the apparatus, such as part of a low-invasive procedure. For example, the apparatus may be positioned in a generally cylindrical barrel or other enclosure such that the apparatus has a reduced cross-sectional condition generally corresponding to an internal chamber of the barrel. The barrel, which can be part of a catheter system or other implantation device, can then be utilized to position the apparatus at a desired location in a patient's heart and to discharge the apparatus from the barrel. Upon being discharged, the apparatus may expand from the reduced cross-sectional condition to an expanded cross-sectional condition, such that an exterior portion of the base engages adjacent tissue of the patient's heart (e.g., at an annulus of the patient's defective or damaged heart valve). This expansion of the apparatus mitigates axial movement of the apparatus relative to the adjacent tissue. The implantation may be performed with or without cardiopulmonary bypass. To reduce the invasiveness of the procedure, the implantation of the apparatus may further be performed without opening the patient's heart.

When the apparatus is implanted at an annulus of a heart valve, the buttress provides surfaces against which two or more leaflets of the patient's heart valve may move into and out of engagement. When the leaflets engage, or coapt with, the buttress, blood flow through the valve is inhibited, thereby mitigating regurgitation (e.g., flow of blood from the ventricle back into the atrium). The apparatus advantageously permits the flow of blood through patient's valve across at least two opposite surfaces of the buttress as the leaflets are urged away from the buttress (e.g., flow of blood from the left atrium into the left ventricle).

To the accomplishment of the foregoing and related ends, the invention comprises the features hereinafter fully described and particularly pointed out in the claims. The following description and the annexed drawings set forth to detail certain illustrative example aspects of the invention. These example aspects are indicative of but a few of the various ways in which the principles of the invention may be employed. Other objects, advantages, and novel features of the invention will become apparent from the following detailed description of example aspects of the invention when considered in conjunction with the drawings.

DETAILED DESCRIPTION

The present invention relates generally to a cardiac prosthesis that cooperates with a patient's heart valve to help improve operation of the heart valve, such as by mitigating prolapse of one or more leaflets. The prosthesis includes at least one axially extending buttress. When the prosthesis is implanted at an annulus of a heart valve, the buttress provides surfaces against which two or more leaflets of the patient's heart valve may move into and out of engagement. When the leaflets engage, or coapt with, the buttress, blood flow through the valve is inhibited, thereby mitigating regurgitation. When the leaflets are urged away from the buttress, the flow of blood is permitted through the prosthesis.

The prosthesis, or apparatus, may also be manipulated to a reduced cross-sectional dimension, such as within an enclosure, to facilitate the positioning of the apparatus during implantation, and then removed from the housing to permit expansion of the apparatus to an expanded cross-sectional dimension at an implantation site. This procedure may be utilized for implanting the apparatus in a generally minimally invasive manner, such as through a catheter or other implantation device. The invasiveness may further be diminished by performing the procedure with little or no cardio-pulmonary bypass.

Figures 1, 2:
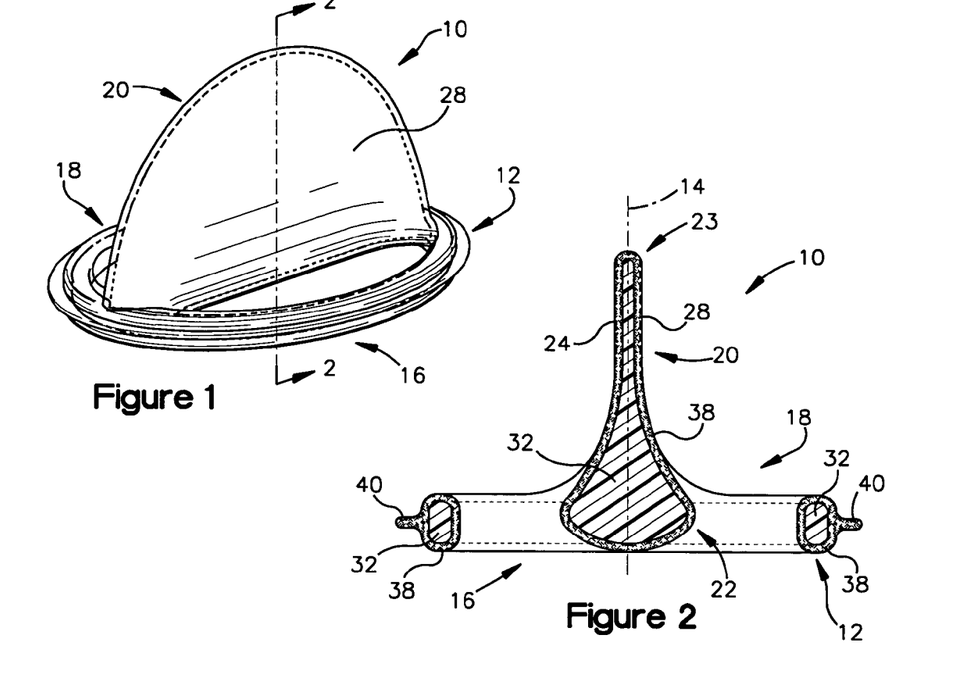
FIG. 1 is an isometric view of an apparatus in accordance with an aspect of the present invention.
FIG. 2 is a cross-sectional view of the apparatus of FIG. 1 taken along line 2—2 in FIG. 1.

FIGS. 1–2 illustrate an apparatus 10, in accordance with an aspect of the present invention, for helping improve operation of a heart valve. The apparatus 10 includes a base portion 12, which may be a curved arc, an oval shape, egg-shaped, or another suitable shape dimensioned and configured for attachment at an annulus of a heart valve. A central axis 14 extends through the apparatus 10 substantially transverse to a plane extending through the base portion 12 and through a center of the base portion. The base portion 12 has an inflow side 16 and an outflow side 18.

The base portion 12 can be formed of rigid or flexible material, depending on the desired amount of support for the valve annulus to which the apparatus 10 is to be mounted. For example, the base portion 12 may be a plastic-like material, a metal, or other material suitable for implantation into a patient. The base portion 12 provides the benefits of an annuloplasty ring (e.g., the base portion helps support a valve annulus at a desired orientation).

The apparatus 10 also includes a buttress 20 that is attached to, and extends axially from, the base portion 12 at one or more locations on the arcuate base portion. The buttress 20 provides surfaces against which leaflets of a heart valve may engage to mitigate prolapse. In the example of FIGS. 1 and 2, the buttress 20 is connected to the base portion 12 at diametrically opposed portions of the base portion and extends axially through a center of the base portion.

By way of example, the apparatus 10 may be implanted at the annulus of a mitral valve of a heart to improve the function of the mitral valve. The posterior leaflet of the mitral valve may engage a first posterior side surface 24 of the buttress 20 and the anterior leaflet of the mitral valve may engage an opposite second anterior side surface 28 of the buttress. The buttress 20 has a base 22 with a first width and a distal end 23 with a second width narrower than the first width (FIG. 2). The base 22 of the buttress 20 defines a curved convex lip on both the posterior and anterior side surfaces 24, 28 near the base portion 12, which lips inhibit prolapse of the respective leaflets. That is, the posterior and anterior side surfaces 24, 28 of the buttress 20 facilitate proper function of the leaflets as during their engagement and disengagement with the side surfaces of the buttress (see, e.g., FIGS. 11 and 12).

The buttress 20 extends axially away from the outflow side 18 of the base portion 12. In the example of the apparatus 10 shown in FIGS. 1–2 (having a complete annular base portion 12), two apertures extend axially through the apparatus 10, one between a first arc length of the base portion 12 and the posterior side surface 24 and another between an opposite second arc length of the base portion and the anterior side surface 28. The apertures provide openings or orifices to permit the passage of blood through the apparatus 10, such as during diastole of a mitral valve. The buttress 20, in conjunction with the leaflets also inhibits the flow of blood when the valve is in a closed position, such as during ventricular contraction at systole.

Figure 3:
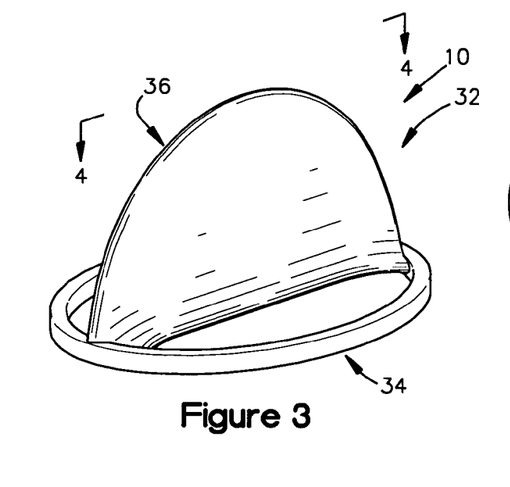
FIG. 3 is an isometric view of a support frame for an apparatus in accordance with another aspect of the present invention.
Figure 4:
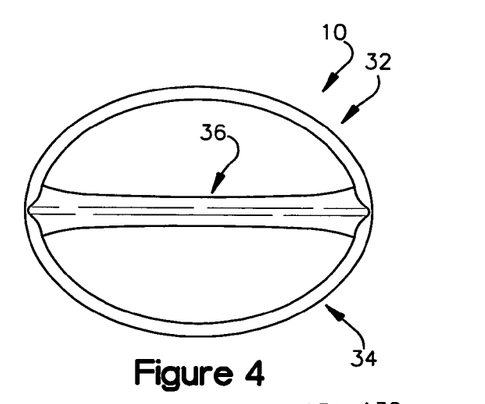
FIG. 4 is a top view of the support frame of FIG. 3 taken along line 4—4 of FIG. 3.

The apparatus 10 shown in FIGS. 1–4 may include an underlying support frame 32 that is dimensioned and configured to provide a desired shape for the apparatus 10. As shown in FIG. 3, the support frame 32 provides a support mechanism that forms the base portion 12 and the buttress 20. The support frame 32 has a frame part 34 for supporting the base portion 12 and a frame part 36 for supporting the buttress 20. The support frame 32 may be formed of a resilient and/or flexible material, such as a plastic, metal, or other biocompatible material suitable for implantation into a human. The rigidity or flexibility of each part of the frame may vary depending upon the amount of support desired at the annulus (by the base portion) as well as the amount of flexibility desired during engagement between the leaflets and the buttress 20.

Alternatively, the support frame 32 may be formed of a substantially inelastically deformable material (e.g., bendable to, and remaining in, a desired shape), such as metal wire. The surgeon implanting the apparatus 10 may thereby orient the buttress 20 and/or the base portion 12 to a desired shape for improving the operation of the valve. Such material also may exhibit sufficient resilience so that it maintains the shape set by the surgeon (or manufacturer) after being implanted and subjected to the dynamics of the heart valve.

In accordance with another aspect of the present invention, the support frame 32 can be sufficiently flexible and resilient to permit the apparatus 10 to be shaped to a reduced cross-sectional dimension during positioning and then to be expanded (e.g., automatically or upon stimulation) to an increased cross-sectional dimension. For example, the apparatus may be implanted within a barrel of an implantation device, such as a catheter for implantation through a vessel or a generally linear implantation system, which may be utilized to implant the apparatus under direct or hidden vision of the surgeon (see, e.g., FIGS. 17 and 18).

The frame part 34 of the base portion 12 and the frame part 36 of the buttress 20 may be formed of the same or different materials depending on the material properties (elasticity, rigidity, resilience, etc.) desired for each part 12, 20 of the apparatus 10.

An outer sheath 38 of a biocompatible material may cover the support frame 32, including the frame part 34 of the base portion 12 and the frame part 36 of the buttress 20. The outer sheath 38 may be substantially any material, such as a cloth-like or fabric material (natural or synthetic) or a biological material, such as collagen or an animal tissue material. An acceptable animal tissue material may be smooth animal pericardium (e.g., equine, bovine, porcine, etc.) that has been tanned or fixed by a suitable tanning environment. The pericardium may also be cross-linked with glutaraldehyde and heparin bonded by a detoxification process. For example, the biological tissue material may be one of the NO-REACT® natural tissue products that are commercially available from Shelhigh, Inc. of Millburn, N.J. The NO-REACT® natural tissue products exhibit improved biocompatibility and mitigate calcification and thrombus formation. The exposed smooth animal pericardium covering the buttress 20 may further inhibit abrasion that could occur in response to engagement and disengagement of the leaflets and the buttress 20.

The apparatus 10 also may include an implantation flange 40 (or sewing ring) that circumscribes the base portion 12 of the apparatus 10 (FIG. 2). The implantation flange 40 extends radially outwardly from the base portion 12 and provides a structure for facilitating implantation of the apparatus 10. The implantation flange 40 may be formed of a flexible material, such a cloth-like or fabric material (natural or synthetic) or a biological material, such as collagen, or an animal tissue material. For example, the implantation flange 40 may be formed of a substantially biocompatible biological material, such as animal tissue (e.g., animal pericardium). The implantation flange 40 may also be formed as an integral part of the outer sheath 38, such as a single or double layer of the material that is used to form the outer sheath.

Figure 5:
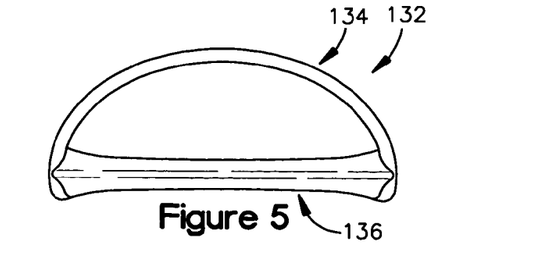
FIG. 5 is a top view of a support frame for an apparatus in accordance with another aspect of the present invention.

FIG. 5 illustrates an underlying support frame 132 in accordance with another aspect of the present invention. As with the support frame 32 of FIGS. 3–4, the support frame 132 may be dimensioned and configured to provide a desired shape for an apparatus. The support frame 132 has a frame part 134 for supporting a base portion and a frame part 136 for supporting a buttress. The support frame 132 provides a support mechanism that forms a base portion and a buttress of an apparatus in accordance with another aspect of the present invention. The support frame 132 may be formed of a resilient and/or flexible material, such as a plastic, metal, or other material suitable for implantation into a human. The rigidity or flexibility of each part of the frame may vary depending upon the amount of support desired at the annulus (by the base portion) as well as the amount of flexibility desired during engagement between the leaflets and the buttress.

Alternatively, the support frame 132 may be formed of a substantially inelastically deformable material (e.g., bendable to and remaining in a desired shape), such as metal wire. The surgeon implanting the apparatus may thereby reorient the buttress and/or the base portion to a desired shape for improving the operation of the valve. Such material also may exhibit sufficient resilience so that it maintains the shape set by the surgeon (or manufacturer) after being implanted and subjected to the dynamics of the heart valve.

In accordance with another aspect of the present invention, the support frame 132 can be sufficiently flexible and resilient to permit the apparatus to be shaped to a reduced cross-sectional dimension during positioning and then to be expanded (e.g., automatically or upon stimulation) to an increased cross-sectional dimension. For example, the apparatus may be implanted within a barrel of an implantation device, such as a catheter for implantation through a vessel or a generally linear implantation system, which may be utilized to implant the apparatus under direct or hidden vision of the surgeon.

The D-shaped frame part 134 of the base portion and the axially extending frame part 136 of the buttress may be formed of the same or different materials depending on the material properties (elasticity, rigidity, resilience, etc.) desired for the base portion and buttress of the apparatus 10.

As with the support frame 32 of FIGS. 1–4, an outer sheath of a biocompatible material may cover the support frame 132, including the frame part 134 of the base portion and the frame part 136 of the buttress. The material can be a treated natural tissue material (e.g., collagen, pericardium, dura matter and the like) or a synthetic material (e.g., fabric, molded collagen and the like), such as described above. An apparatus utilizing the support frame 132 may also include an implantation flange that circumscribes the D-shaped base portion of the apparatus.

Figures 6, 7:
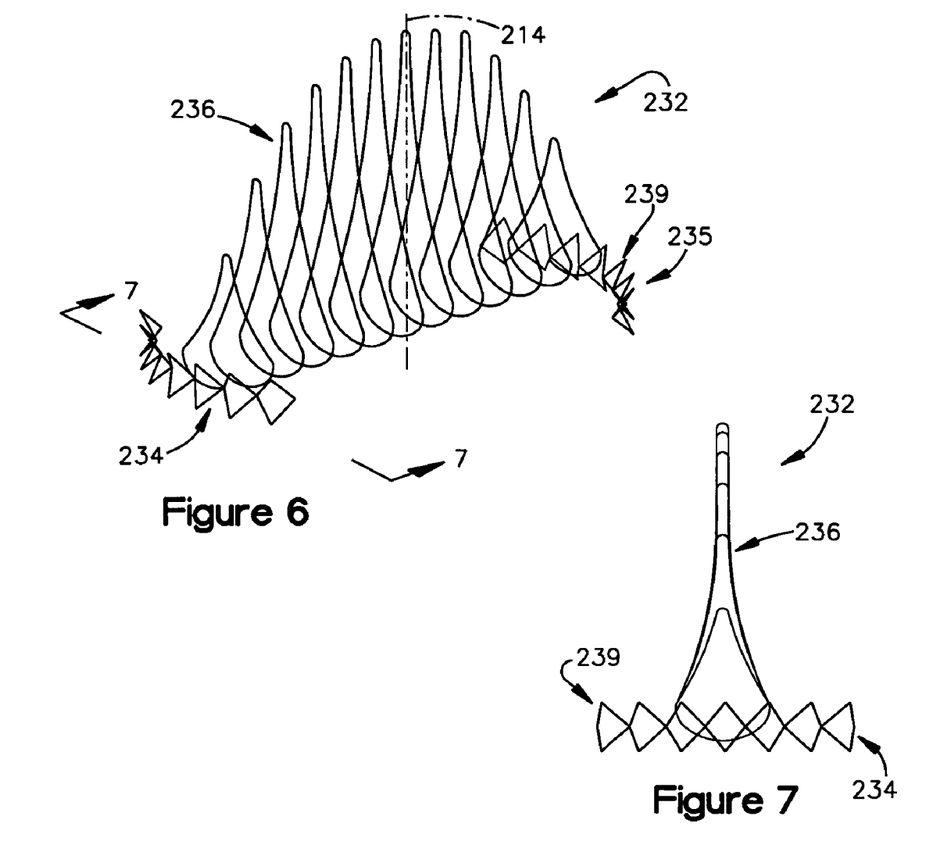
FIG. 6 is an isometric view of a support frame for an apparatus in accordance with another aspect of the present invention.
FIG. 7 is an end view of the support frame of FIG. 6 taken along line 7—7 of FIG. 6.

FIGS. 6 and 7 show an example of a support frame (or base portion) 232 in accordance with another aspect of the present invention. The support frame 232 may be dimensioned and configured to provide a desired contour for the apparatus. In this example, the support frame 232 includes two separate arc portions 234, 235 each having a coincident central axis 214. A buttress portion 236 connects the arc portions 234, 235 and extends axially from the arc portions 234, 235 generally parallel to the axis 214.

According to another aspect of the present invention, the support frame 232 may be deformable between reduced and expanded cross-sectional conditions, as discussed above. The support frame 232 is formed of a wire or filament configured as a mesh or weave to provide the desired variability of the cross-sectional dimension. The mesh may be a metal, an alloy, or other suitable material that will maintain its configuration and, in turn, help anchor the apparatus at a desired position when implanted.

By way of example, the mesh may be formed of a shape memory alloy material, such as a nitinol (nickel-titanium alloy) wire. Shape memory (or thermal memory) is a characteristic in which a deformed part remembers and recovers to a pre-deformed shape upon heating. By forming the support frame 232 of a shape memory alloy, the support frame is inelastically deformable to new shapes, such as to a reduced cross-sectional dimension, when in its low-temperature, or martensitic, form. Thus, the support frame may be cooled, such as by cool water, and then compressed to its reduced cross-sectional condition.

When the support frame 232 is heated to its transformation temperature, which may vary according to the alloy composition, the support frame reverts to its high-temperature, or austenitic, form. An apparatus that utilizes the support frame 232 thus may retain the compressed condition by keeping the support frame cooled. Alternatively, the support frame 232 may be retained in the compressed position by sutures, other mechanical retaining features circumscribing the structure, a cylindrical enclosure around the structure, etc. The support frame 232 and associated apparatus will then return toward a high-temperature (or original) shape upon removal of the retaining elements (not shown).

It is to be appreciated that, alternatively, the support frame 232 may be inelastically deformable so as to require an intervening force or a stimulus (e.g., other than temperature) to return the deformed support frame to a desired expanded shape. For example, a balloon catheter, spring mechanism, or electrical current may be employed to urge the support frame 232 and associated apparatus to an expanded shape so that, after being implanted at a desired location, the support frame engages the surrounding tissue in a manner to inhibit movement relative to the surrounding tissue. Alternatively, the support frame 232 may be a resilient material that seeks to return to its original expanded state.

The support frame 232 may also include spikes (or protrusions) 239 extending generally radially outwardly from the arc portions 234, 235. The spikes 239 may be formed as one or more rows spaced axially apart. The spikes 239 may be oriented in varied relationships as is desired for a particular implantation site. Similar to all embodiments shown and described herein, the support frame can be covered with a biologically compatible material, such as one or more sheets of a natural or synthetic material, such as described above.

Figure 8:
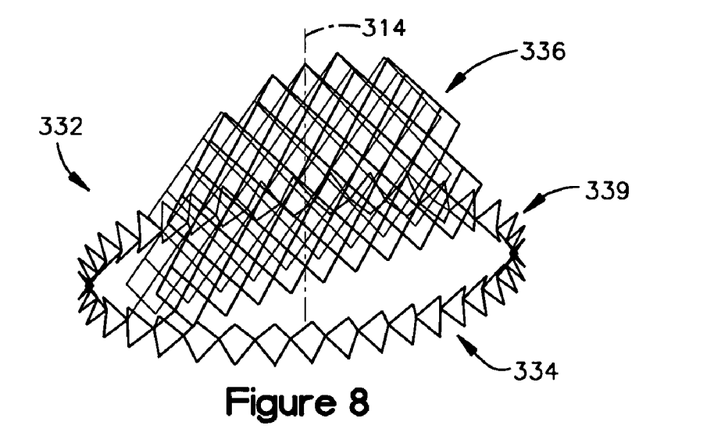
FIG. 8 is an isometric view of a support frame for an apparatus in accordance with another aspect of the present invention.

FIG. 8 shows an example of another support frame 332 in accordance with another aspect of the present invention. The support frame 332 may be dimensioned and configured to provide a desired contour for the apparatus. In this example, the support frame 332 includes an annular base potion 334 having a central axis 314 and a buttress portion 336 extending axially from the base portion 334. It is to be appreciated that the particular configuration of base portion in FIG. 8 can any of those described herein, as the different embodiments are provided for purposes of example and not by way of limitation.

The support frame 332 may be deformable between reduced and expanded cross-sectional conditions, as discussed above. The support frame 332 is formed of a wire or filament configured as a mesh or weave to provide the desired variability of the cross-sectional dimension. The mesh may be a metal, an alloy, or other suitable material that will maintain its configuration and, in turn, help anchor the support frame 332 and associated apparatus at a desired position when implanted.

By way of example, the mesh may be formed of a shape memory alloy material, such as a nitinol wire. By forming the support frame 332 of a shape memory alloy, the support frame is inelastically deformable to new shapes, such as to a reduced cross-sectional dimension, when in its low-temperature, or martensitic, form. Thus, the frame may be cooled, such as by cool water, and then compressed to its reduced cross-sectional condition.

When the support frame 332 is heated to its transformation temperature, which may vary according to the alloy composition, the support frame reverts to its high-temperature, or austenitic, form. An apparatus that includes the support frame 332 thus may retain the compressed condition by keeping the support frame cooled. Alternatively, the support frame 332 may be retained in the compressed position by sutures, other mechanical retaining features circumscribing the structure, a cylindrical enclosure around the structure, etc. The support frame 332 and associated apparatus will then return toward a high-temperature (or original) shape upon removal of the retaining elements.

It is to be appreciated that, alternatively, the support frame 332 can be inelastically deformable so as to require an intervening force or a stimulus (e.g., other than temperature) to return the deformed support frame and associated to a desired expanded shape. For example, a balloon catheter, spring mechanism, or electrical current may be employed to urge the support frame 332 and associated apparatus to an expanded shape so that, after being implanted at a desired location, the support frame engages the surrounding tissue in a manner to inhibit movement relative to the surrounding tissue. As another alternative, the support frame 332 may be a resilient material that seeks to return to its original expanded state.

The support frame 332 may include spikes (or protrusions) 339 extending generally radially outwardly from the arc portions 334. The spikes 339 may be formed as one or more rows spaced axially apart. The spikes 339 may be oriented in varied relationships as is desired for a particular implantation site. It is to be understood that the frame 332 can be covered with one or more sheets of a biocompatible material to provide a prosthesis according to an aspect of the present invention. The biocompatible material can be a treated natural tissue material (e.g., collagen, pericardium, dura matter and the like) or a synthetic material (e.g., fabric, molded collagen and the like), such as described above.

Figure 9:
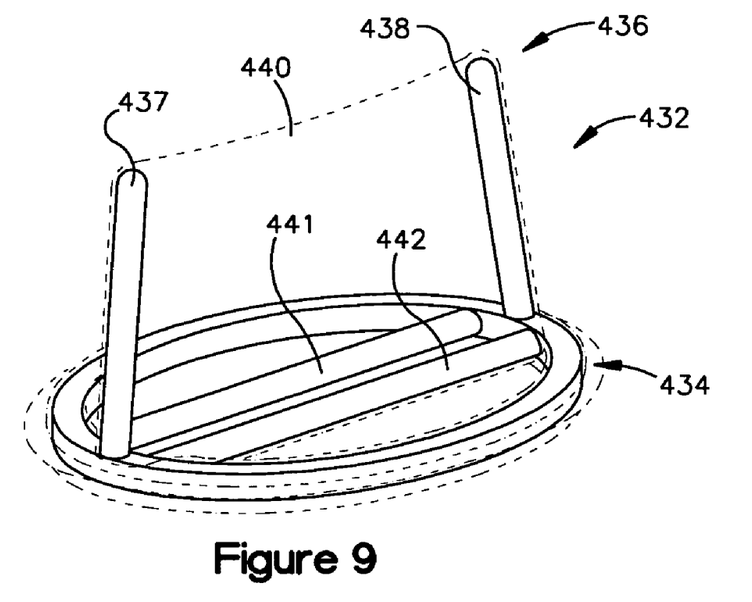
FIG. 9 is an isometric view of a support frame for an apparatus in accordance with another aspect of the present invention.

FIG. 9 shows another example of a support frame 432 that may be utilized to form an apparatus in accordance with another aspect of the present invention. The support frame 432 may include an annular base 434 and a buttress 436 including posts 437, 438 extending axially from the base 434 at diametrically opposed locations. The support frame 432 further includes two chordal members 441, 442 extending between opposed parts of the base 433, generally interconnecting the locations from which the posts 437, 438 extend. These chordal members 441, 442 define a wider lip for the base of the buttress similar to the base 22 of the apparatus 10 (FIG. 2), which helps mitigate prolapse of associated leaflets when the apparatus is implanted. The posts 437, 438 may be formed of the same material as the base 434 (e.g., an integrated frame). Alternatively, the posts 437, 438 may be formed of different materials than the base 434 and may be attached to the base 434 by any suitable fastening means. An outer sheath 440 may surround the support frame 432, as discussed above.

Figure 10:
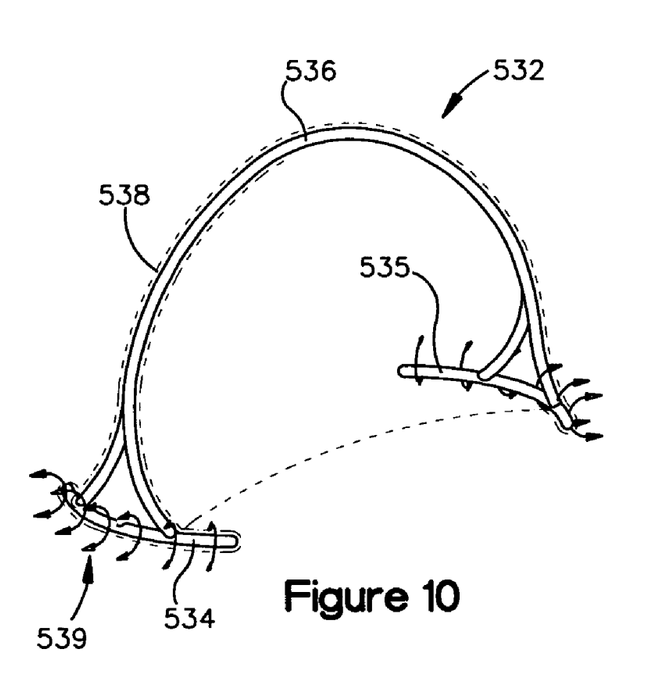
FIG. 10 is an isometric view of a support frame for an apparatus in accordance with another aspect of the present invention.

FIG. 10 shows yet another example of a support frame 532 that can be utilized to form an apparatus in accordance with another aspect of the present invention. The support frame 532 may include two arc portions 534, 535 that define a base and an arc shaped buttress 536 extending axially from and interconnecting each arc portion 534, 535. The buttress 536 may be formed of the same material as the arc portions 534, 535 (e.g., an integrated frame). Alternatively, the buttress 536 may be formed of different materials from the arc portions 534, 535 and may be attached to the arc portions 534, 535 by any suitable fastening means.

C-shaped spikes 539, which extend radially outward from the arc portions 534, 535, may protrude through an outer sheath 538 such as along a perimeter of the arc portions. The outer sheath can be formed of one or more sheets of a biocompatible material, such as a treated natural tissue material (e.g., collagen, pericardium, dura matter and the like) or a synthetic material (e.g., fabric, molded collagen and the like), such as described herein. The spikes 539 may help maintain the support frame 532 and associated apparatus at a desired location when implanted. Different portions of the spikes may be provided in different lengths in order to enhance securement and mitigate damage to surrounding tissue. For example, a portion of the spikes 539, such as those near ends of the arc portions 534, 535, may be shorter than those extending from between the ends of the arc portions. Thus, the shorter spikes may be aligned and inserted a lesser amount into surrounding tissue yet still help maintain a desired location for the apparatus. Longer spikes may be aligned and inserted into tissue that can better accommodate longer spikes.

Figure 11:
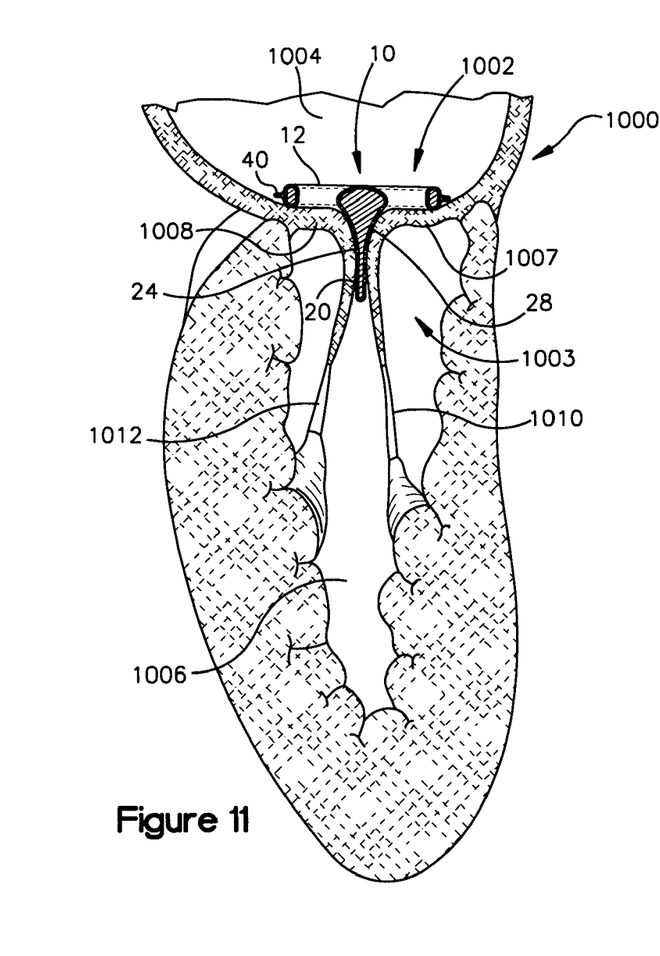
FIG. 11 is a cross-sectional view of part of a heart in which an apparatus, in accordance with an aspect of the present invention, is mounted, illustrating a first condition of a heart valve.
Figure 12:
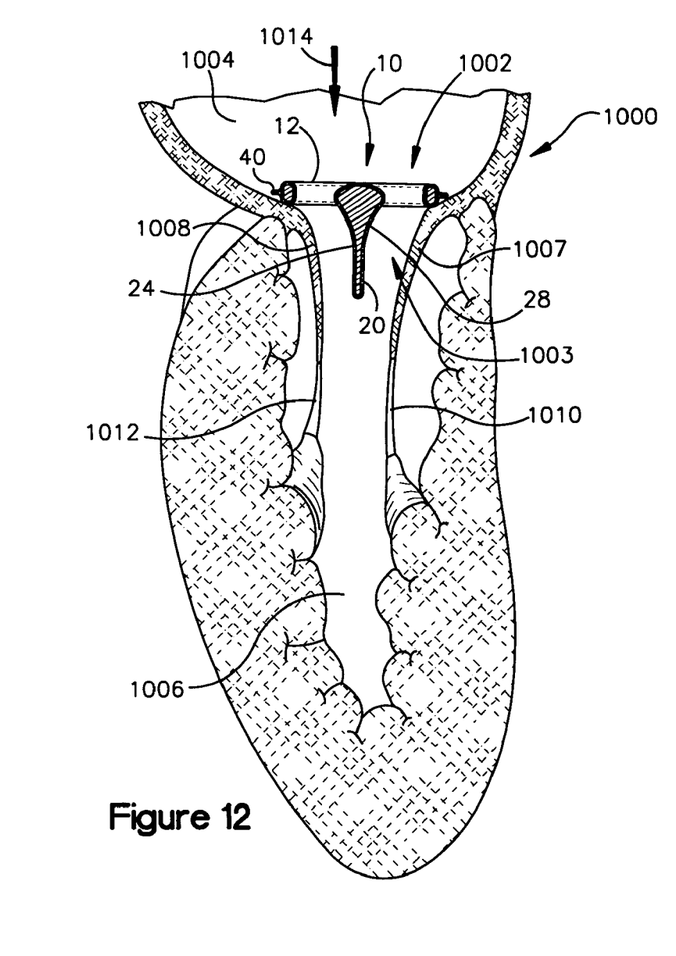
FIG. 12 is a cross-sectional view of the heart and apparatus of FIG. 11 illustrating a second condition of the heart valve.

FIGS. 11 and 12 illustrate part of a heart 1000 in which an apparatus, such as the apparatus 10 illustrated with respect to FIGS. 1–2, is implanted at an annulus 1002 of a mitral valve 1003. The mitral valve 1003 is intended to provide unidirectional flow of blood from the left atrium 1004 into the left ventricle 1006. The mitral valve 1003 includes a posterior leaflet 1007 and an anterior leaflet 1008. The posterior leaflet 1007 extends from the annulus 1002 opposite the aortic opening (not shown) and attaches to the muscular tissue of the left ventricle wall by fibrous cordae tendinae 1010. The anterior leaflet 1008 extends from the annulus 1002 adjacent the aortic opening (not shown) and attaches to the muscular tissue of the left ventricle wall by fibrous cordae tendinae 1012.

As mentioned above as an example, the apparatus 10 may include an implantation flange 40 that can be sutured to the fibrous tissue (e.g., the valve wall) at the annulus 1002 of the valve 1003. The buttress 20 may extend from the base 12 of the apparatus 10 into the left ventricle 1006 at a position between the posterior leaflet 1007 and the anterior leaflet 1008.

It is to be appreciated that the buttress 20 may be formed of a generally rigid material that remains substantially stationary (e.g., static) during both systole and diastole. Alternatively, the buttress 20 may be formed of sufficiently flexible material, such as a sheet of material supported in a peripheral frame (see, e.g., FIGS. 9–10) or by employing a more flexible type of frame to permit movement thereof commensurate with the flow of blood from the left atrium 1004 into the left ventricle 1006 through the mitral valve 1003.

FIG. 11 illustrates the mitral valve 1003 is in a closed position (at systole), in which the posterior leaflet 1007 engages the posterior surface 28 of the buttress 20 and the anterior leaflet 1008 engages the anterior surface 24 of the buttress 20 in accordance with the aspect of the present invention illustrated by the apparatus 10. The buttress 20 of the apparatus 10 thereby provides surfaces against which the posterior leaflet 1007 and the anterior leaflet 1008 coapt. As a result, the buttress 20, the posterior leaflet 1007, and the anterior leaflet 1008 cooperate to mitigate prolapse of such leaflets. This, in turn, inhibits regurgitation of blood from the left ventricle 1008 into the left atrium 1006, such as during ventricular contraction at systole.

As shown in FIG. 12, the buttress 20, in conjunction with the posterior leaflet 1007 and the anterior leaflet 1008, also facilitates and promotes unidirectional flow of blood at diastole, such as shown in FIG. 12 by arrow 1014. In particular, an opening or aperture extends through the implanted apparatus 10 between both the buttress 20 and the posterior leaflet 1007 and the buttress 20 and the anterior leaflet 1008, as stated above. Advantageously, the movement of the posterior and anterior leaflets 1007, 1008 relative to the buttress 20, in response to the flow of blood during diastole, provides a sufficient orifice to permit the free flow of blood from the left atrium 1004 into the left ventricle 1006. The annular base portion 12 of the apparatus 10 also may help support the annulus 1002 of the mitral valve 1003 at systole to promote the desired coaptation between the buttress 20 and the posterior and anterior leaflets 1007, 1008 and also further help prevent prolapse (FIG. 11).

Figure 13:
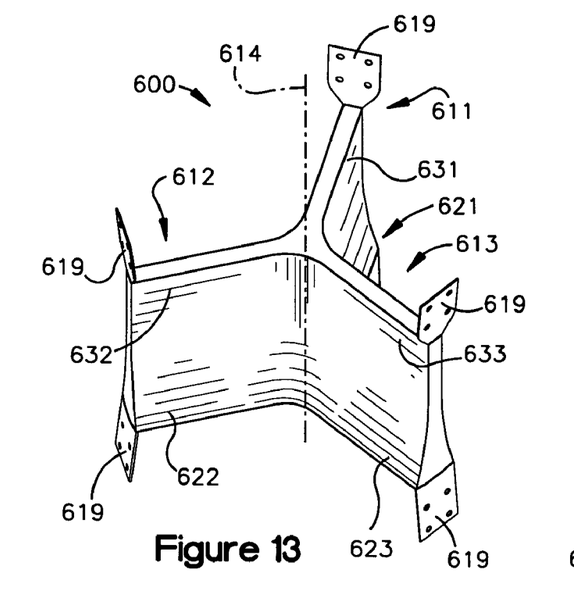
FIG. 13 is an isometric view of an apparatus in accordance with another aspect of the present invention.
Figure 14:
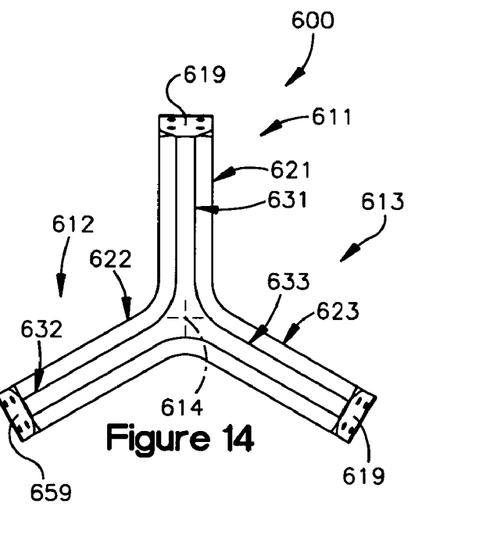
FIG. 14 is a top view of the apparatus of FIG. 13.

FIGS. 13 and 14 show an apparatus 600 in accordance with another aspect of the present invention. The apparatus 600 may perform a similar function for a tricuspid valve that the apparatus 10 does for a bicuspid valve. The apparatus 600 includes a buttress having three buttress portions 611, 612, 613 extending radially from a central axis 614. Each buttress portion 611, 612, 613 has a widened base portion 621, 622, 623 and a narrower opposite distal portion 631, 632, 633 (e.g., at its outflow end). The wider base portions 621, 622, 623 also include lip portions at the inflow end thereof that facilitate the engagement and disengagement of the buttress portions 611, 612, 613 and the leaflets of the tricuspid valve, similar to the buttress 620 of the apparatus 10. For example, the widened lip at the inflow end mitigate prolapse of the leaflets. The apparatus 600 further includes flanges 619 for securing the apparatus to surrounding tissue, such as by suturing. The apparatus 600 may also include an underlying support frame and outer sheath, as discussed above in FIGS. 1–10.

Figure 15:
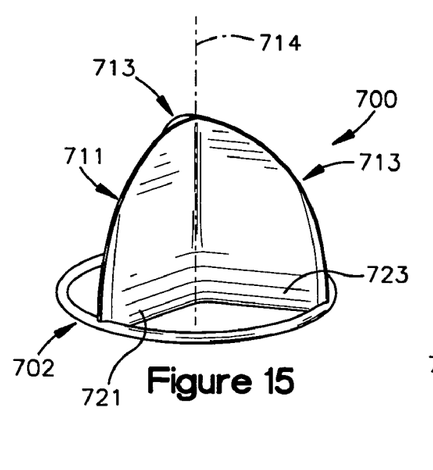
FIG. 15 is an isometric view of an apparatus in accordance with another aspect of the present invention.
Figure 16:
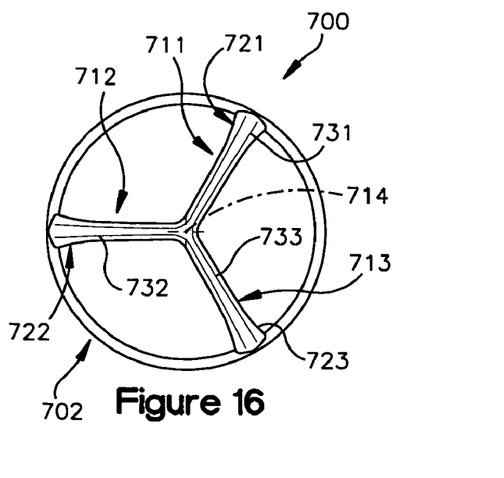
FIG. 16 is a top view of the apparatus of FIG. 15.

FIGS. 15 and 16 show an apparatus 700 in accordance with another aspect of the present invention. The apparatus 700 may perform a similar function for a tricuspid valve that the apparatus 600 does for a tricuspid valve and the apparatus 10 does for a bicuspid valve. The apparatus 700 includes three buttress portions 711, 712, 713 extending radially from a central axis 714. Each buttress portion 711, 712, 713 also extends axially from an annular base portion 702. The base portion 702 may be circular, oval, C-shaped, or other suitable shape. Each buttress portion 711, 712, 713 has a widened base 721, 722, 723 adjacent the base portion 702 and a narrower opposite distal portion 731, 732, 733. The wider bases 721, 722, 723 form lips that facilitate the engagement and disengagement of the buttresses 711, 712, 713 and the leaflets of the tricuspid valve, similar to the buttresses 611, 612, 613 of the apparatus 600 and the buttress 20 of the apparatus 10. For example, the widened lip at the inflow end of the buttress portions 711, 712, 713 mitigate prolapse of the leaflets. The apparatus 700 may also include an underlying support frame and outer sheath, as discussed above in FIGS. 1–10.

Figure 17:
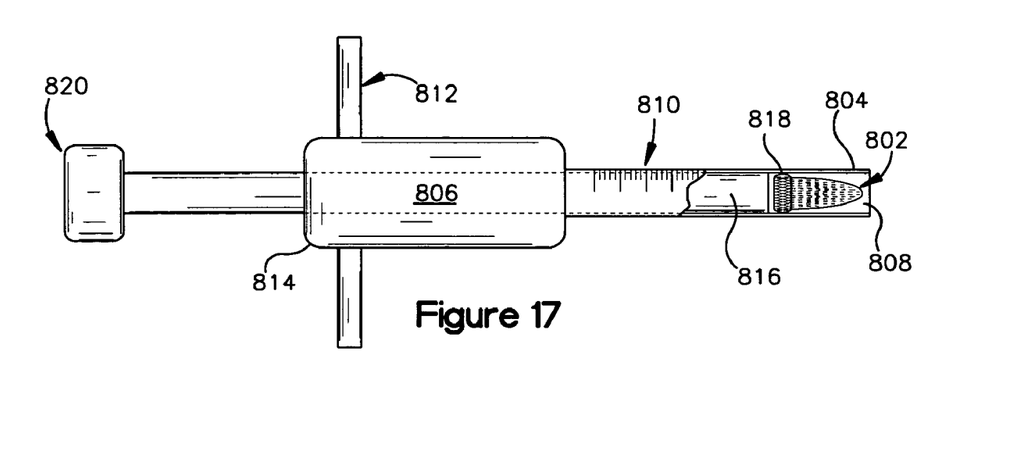
FIG. 17 is an example implantation mechanism for use with an apparatus in accordance with the present invention.

FIG. 17 illustrates an implanter apparatus 800 for implanting an apparatus 802 in accordance with an aspect of the present invention, such as to facilitate sutureless or low invasive implantation of the apparatus. It is to be understood and appreciated that the apparatus 802 may be any of the apparatuses shown and/or described herein and may be implanted with such an implantation apparatus 800. The implanter apparatus 800 includes an elongated cylindrical barrel 804 that extends from a body portion 806 and terminates in an open end 808. The barrel 804 has an inner diameter that is less than the outer diameter of the apparatus 802 in its expanded condition. Thus, in order to insert the apparatus 802 into the barrel 804, the apparatus is deformed to a reduced cross-sectional dimension, such as at about one-half or less than its fully expanded condition.

For example, the inner diameter of the barrel 804 may range from about 5 mm to about 15 mm, whereas the outer diameter of the apparatus 802 (in its expanded condition) typically may range from about 15 mm to about 40 mm. Thus, the barrel 804 may accommodate an apparatus 802 which has been deformed to reduced cross-sectional dimension. The exterior of the barrel 804 further may include indicia (e.g., ruler markings) 810 that can help indicate the distance the barrel is inserted into a patient.

The implanter apparatus 800 also includes a handle 812 that extends outwardly from a proximal end 814 of the body portion 806. The handle 812, which may be gripped by a surgeon, facilitates manipulating the barrel 804 along a desired path. A plunger 816 has a distal end 818 that can be urged into engagement with the apparatus 802 to push the apparatus from the opening 808 of the barrel 804 for implantation. The plunger 816 includes an elongated portion that extends from its distal end 818 and terminates in a proximal end portion 820. The proximal end portion 820 may operate as a trigger that can be grasped by a surgeon to move the plunger 816 through the barrel 804. Other means to discharge the apparatus 802 also could be utilized in accordance with an aspect of the present invention. Fluid, such as saline, also may be introduced into the barrel 804, such as through an opening (not shown) in the plunger 816, to facilitate the discharge of the apparatus 802 from the barrel.

The implanter apparatus 800 may be introduced into a blood vessel (e.g., the pulmonary artery or aorta) that provides a substantially direct and linear path to the desired implantation location. Further, utilizing the implanter apparatus 800, a procedure may be implemented without cardiopulmonary bypass, such as when the apparatus 802 is implanted through the pulmonary artery or directly through the patient's heart muscle (e.g., through the anterior wall of the patient's right ventricle). Alternatively, cardiopulmonary bypass may be used, but advantageously for only a generally short period of time, such as when the apparatus is implanted at the aortic position. Bypass generally is required when implanting at the aortic location due to the relatively high blood pressure, as well as to decalcify the patient's existing heart valve, if needed.

By way of further example, a low invasive minithoracotomy may be used to crate a passage for access to the heart of the patient and then a surgeon may insert the barrel 804 of the implanter apparatus 800 through the passage. The surgeon may further be guided by an appropriate vision system to help guide the barrel 804 to a desired location for implanting the apparatus 802, such as through a blood vessel or directly through the heart muscle. As stated above, it will further be appreciated that such a procedure may be implemented with little or no cardiopulmonary bypass.

Figure 18:
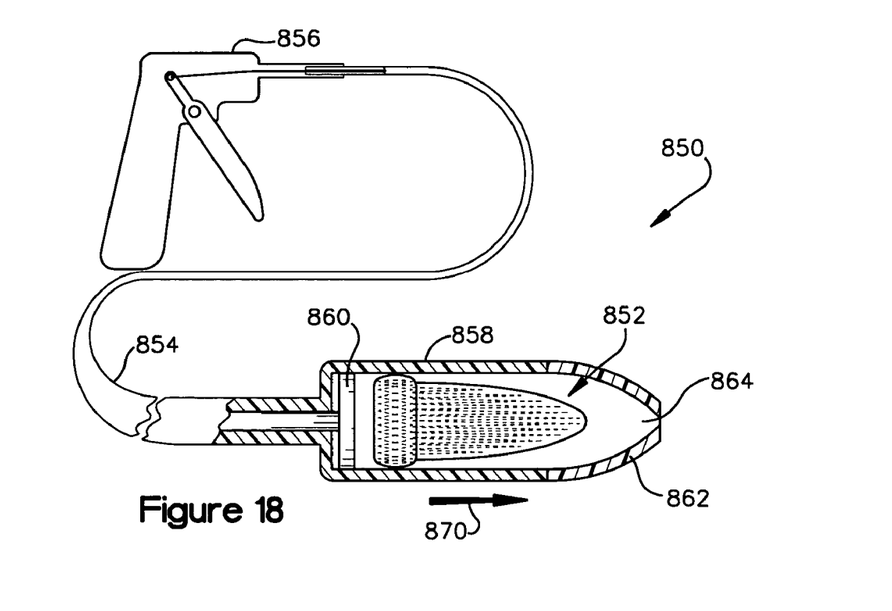
FIG. 18 is another example implantation mechanism for use with an apparatus in accordance with the present invention.

FIG. 18 illustrates a variation of an implantation apparatus 850 that may be utilized to implant an apparatus 852 in accordance with an aspect of the present invention. It is to be understood and appreciated that the apparatus 852 may be any of the apparatuses shown and/or described herein. For purposes of example, an apparatus 852 has a generally annular base portion is shown in FIG. 18.

The implantation apparatus 850 may be in the form of a catheter system. The implantation apparatus 850 includes an elongated connecting element 854 extending between a trigger mechanism 856 and an enclosure 858, in which the apparatus 852 is located. At least a portion of the apparatus 852 is located within the enclosure 858. A plunger mechanism 860 is located at a proximal end of the enclosure 858 for urging the apparatus 852 generally axially from the enclosure 858. An opposite end 862 of the enclosure 858 may be formed of a pliable material or a plurality of moveable members that may open as the apparatus 852 is urged through an opening 864 located at a distal end. It is to be appreciated that the length of the connecting element 854 may vary according to where the apparatus 852 is to be implanted and the method of implantation. The enclosure 858 may also be rotatable about its longitudinal axis to facilitate proper angular orientation of the apparatus 852 during implantation at the patient's heart valve.

The apparatus 852 is illustrated within the enclosure 858 as having its reduced cross-sectional condition, as stated above. The apparatus 852 within the enclosure 858 has a cross-sectional dimension that is less than its normal (or expanded) cross-sectional dimension, being maintained in such position by the enclosure. Those skilled in the art will appreciate that the orientation of the inflow and outflow ends of the apparatus 852 may vary depending upon the direction in which blood is to flow through the valve when implanted.

The compression of the apparatus 852 and insertion into the enclosure 858 may be performed just prior to surgery. The plunger mechanism 860 may be urged in the direction of arrow 870, such as by activating the trigger 856. Movement of the plunger 860, in turn, may cause the apparatus 852 also to be moved in the direction of the arrow 870 within the enclosure 858. As the apparatus 852 is urged through the opening 864 and discharged therefrom, the apparatus may expand, either automatically or upon a stimulus (e.g., temperature, electrical energy, or cutting a mechanical retaining element around the apparatus). Accordingly, the opening 864 should be positioned at the location where the apparatus 852 is to be implanted prior to being discharged. When the apparatus 852 expands, the sidewall of the base portion and/or associated spikes may engage and/or penetrate into surrounding tissue so as to mitigate axial movement and rotation of the apparatus relative to the surrounding tissue and the patient's valve at which the apparatus is implanted. As a result, the apparatus 852 may be implanted without sutures to cooperate with the patient's valve (which can be the patient's original valve or a replacement valve) to provide a competent valve in accordance with an aspect of the present invention. The apparatus 852 may be implanted either as part of an open chest procedure or the patient's chest may be closed.

Those skilled in the art will understand and appreciate that any of the apparatuses 10, 600, 700 and associated support frames 32, 132, 232, 332, 432, 532 shown and described herein may be implanted using either of the implantation devices 800, 850. It further is to be appreciated that other configurations of implantation devices could also be utilized to implant such apparatuses according to the aspects of the present invention.

In view of the foregoing, an apparatus according to the present invention provides a useful repair apparatus for helping to improve operation of a patient's heart valve. The apparatus may be employed to both support a heart valve annulus and mitigate problems associated with coaptation and/or lesions in a leaflet by providing a buttress with which two or more leaflets may move into and out of engagement. The apparatus further provides a simplified repair option (implanting a device at an annulus of a heart valve) when compared with other, more conventional methods of reconstruction and repair.

Additionally, a generally sutureless implantation of the apparatus may be implemented. This can be done with little or no cardio pulmonary bypass, such as may depend on the condition of the patient. By way of example, where a patient experiences sudden regurgitation resulting in severe pulmonary edema, pulmonary bypass may not be an acceptable option. In such circumstances, a minithoracotomy can be performed to provide an opening for positioning a barrel of an implantation device at a desired position in the patient's heart and, in turn, to implant an apparatus in accordance with an aspect of the present invention. The apparatus may provide a permanent or temporary solution, such as to stabilize the patient until the patient can better withstand the stresses of more rigorous surgery, such as a cardio pulmonary bypass. As a result, a significant amount of time may be saved with less stress on the patient, thereby mitigating the risks of morbidity and mortality associated with open-heart surgery typically employed to implant a heart valve prosthesis.

It is to be appreciated by those skilled in the art that, while the illustrated examples show apparatuses for treating a bicuspid (mitral) and tricuspid valves, an apparatus in accordance with the present invention may also be used for repairing other types of heart valves. In addition, an apparatus in accordance with the present invention may be implanted from either the inflow side or outflow side of a heart valve annulus.

What has been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising."

What is claimed is:

1. An apparatus for helping improve operation of a heart valve, comprising:
    a generally annular shaped base portion having a central axis; and
    a buttress extending from the base portion axially relative to the base portion and interconnecting diametrically opposite locations on the base portion, the buttress having at least a first surface and an opposite second surface, the first surface being dimensioned and configured to be engaged by a first leaflet of the heart valve when the apparatus is implanted in the heart valve, the second surface being dimensioned and configured to be engaged by a second leaflet of the heart valve when the apparatus is implanted in the heart valve, whereby the buttress permits flow of blood adjacent the first surface of the buttress and the second surface of the buttress when the first and second leaflets are not engaging the buttress.

2. The apparatus of claim 1, the buttress having a plane of symmetry passing through the central axis of the base portion.

3. The apparatus of claim 1, further comprising an outer sheath of a substantially flexible material covering at least the first and second surfaces of the buttress.

4. The apparatus of claim 3, the outer sheath completely covering the buttress and the base portion.

5. The apparatus of claim 3, wherein the flexible material comprises a substantially biocompatible animal tissue material.

6. The apparatus of claim 5, the biocompatible animal tissue material comprises animal pericardium.

7. The apparatus of claim 3, further comprising a plurality of features extending through the outer sheath generally radially from the base portion to help maintain the apparatus at a desired position relative to the heart valve when the apparatus is implanted in the heart valve.

8. The apparatus of claim 1, the base portion being formed of a shape memory alloy material operative to urge the apparatus to an expanded cross-sectional dimension.

9. The apparatus of claim 1, further comprising features that extend outwardly from the base portion to help maintain the apparatus at a desired position and orientation relative to the heart valve when the apparatus is implanted in the heart valve.

10. The apparatus of claim 9, the base portion being formed of a mesh material with triangular projections at inflow and outflow ends of the base portion, the triangular projections extending outwardly from the base portion to define the features.

11. The apparatus of claim 9, the features extending different lengths from the base portion according to relative positions of the features along the base portion.

12. The apparatus of claim 1, further including a retaining member to retain the apparatus in a reduced cross-sectional condition for facilitating implantation of the apparatus in the heart valve.

13. The apparatus of claim 1, the buttress further comprising a lip portion adjacent the base portion, the lip portion having a width that is greater than a width of a distal portion of the buttress that is spaced axially apart from the lip portion.

14. An apparatus for helping improve operation of a heart valve, comprising:
    a base portion having a central axis; and
    a buttress extending axially from the base portion relative to the base portion, the buttress including a first surface and an opposite second surface, the first surface being dimensioned and configured to be engaged by a first leaflet of the heart valve when the apparatus is implanted in the heart valve, the second surface being dimensioned and configured to be engaged by a second leaflet of the heart valve when the apparatus is implanted in the heart valve, the buttress permitting flow of blood adjacent the surface of the buttress when the leaflet is not engaging the buttress,
    the buttress having a base and an axially opposite distal end, the base having a width, the distal end having a width less than the width of the base, the surface extending between the base and the distal end, the surface including an arcuate lip portion adjacent the base.

15. The apparatus of claim 14, the buttress having a plane of symmetry passing through the central axis of the base portion.

16. The apparatus of claim 14, the buttress permitting flow of blood adjacent both at least the first surface of the buttress and the second surface of the buttress when the first and second leaflets are not engaging the buttress.

17. The apparatus of claim 16, the lip portion including a first lip portion on the first surface of the buttress and a second lip portion on the second surface of the buttress.

18. The apparatus of claim 17, the first and second lip portions facilitating engagement and disengagement of the first and second leaflets and the first and second surfaces of the buttress.

19. The apparatus of claim 14, the base portion comprising a substantially C-shaped base portion having a length between opposed ends of the C-shaped base portion that is curved about the central axis, the buttress extending from an arc portion of the C-shaped base portion intermediate the opposed ends.

20. An apparatus for helping improve operation of a heart valve, comprising:

a generally arcuate base portion having a central axis that extends through the apparatus; and a buttress extending axially from the base portion, the buttress including at least two generally opposing surfaces that extend axially from a base of the buttress, which base extends between and interconnects spaced apart locations of the base portion, and that terminates in a distal end spaced axially apart from the base of the buttress, each of the at least two generally opposing surfaces being dimensioned and configured to be engaged by respective leaflets of the heart valve when the apparatus is implanted in the heart valve, whereby the buttress permits flow of blood along the at least two generally opposing surfaces of the buttress when the leaflets are not engaging the buttress.

21. The apparatus of claim 20, wherein the at least two generally opposing surfaces are spaced apart from each other a distance that defines lip portion of the buttress having a first width at an axial location adjacent the base of the buttress, the first width being greater than a width of the buttress adjacent the distal end of the buttress.

22. The apparatus of claim 20, further comprising a substantially flexible material that covers the at least two generally opposing surfaces of the buttress.

23. The apparatus of claim 20, further comprising an implantation flange that circumscribes and extends radially outwardly from at least a portion of the base portion.

* * * * *